US00PP28348P2

(12) United States Plant Patent
Nir

(10) Patent No.: US PP28,348 P2
(45) Date of Patent: Aug. 29, 2017

(54) ***CHAMELAUCIUM* PLANT NAMED 'REY'**

(50) Latin Name: *Chamelaucium uncinatum×Verticordia grandis*
Varietal Denomination: REY

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 14/999,344

(22) Filed: Apr. 25, 2016

(51) Int. Cl.
*A01H 5/02* (2006.01)

(52) U.S. Cl.
USPC ..... Plt./229

(58) Field of Classification Search
USPC ..... Plt./229
See application file for complete search history.

*Primary Examiner* — Annette Para
(74) *Attorney, Agent, or Firm* — Cassandra Bright

(57) ABSTRACT

A new and distinct *Chamelaucium* cultivar named 'REY' is disclosed, characterized by bright pink flowers with distinctive ciliate sepals. Foliage is lanceolate. The new variety is a *Chamelaucium×Verticordia*, normally producing cut flower stems, or as a garden or container plant.

2 Drawing Sheets

Figure 1:
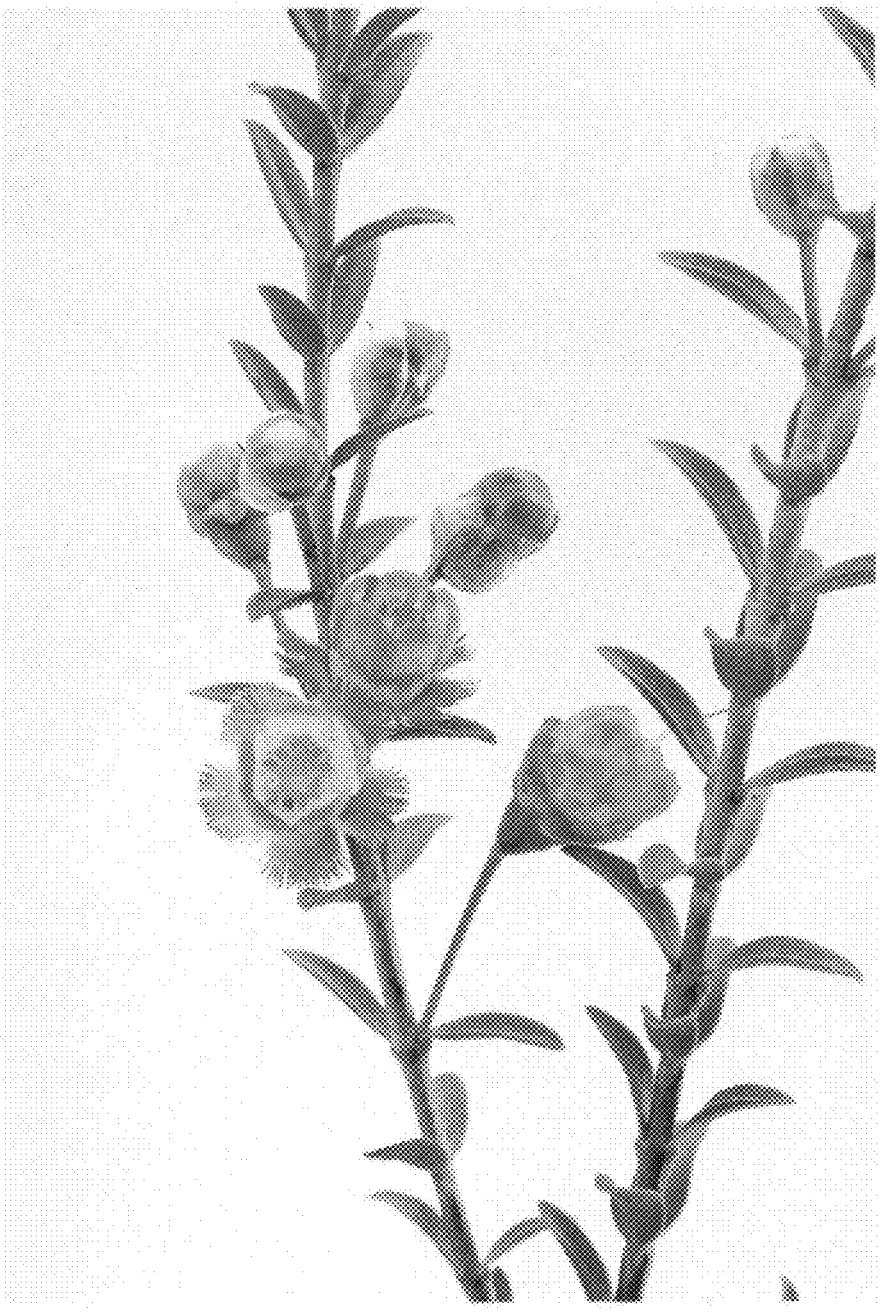

Latin name of the genus and species: *Chamelaucium uncinatum×Verticordia grandis.*

Variety denomination: 'REY'.

BACKGROUND OF THE INVENTION

The new *Chamelaucium×Verticordia* cultivar is the product of a planned breeding program conducted by the inventor, Nitzan Nir, in Kfar Hess, Israel. The objective of the breeding program was to produce new varieties for ornamental commercial applications. The new variety was selected as a seedling from the breeding program at a commercial nursery in Kfar Hess, Israel.

The crossing resulting in this new variety was made in February of 2010. The seed parent is an unnamed *Chamelaucium uncinatum*. The pollen parent is an unnamed *Verticordia grandis*. The new variety was discovered in April of 2011 by the inventor in a group of seedlings resulting from previously mentioned crossing, in a commercial nursery in Kfar Hess, Israel.

Asexual reproduction of the new cultivar has been performed by terminal vegetative cuttings. This was first performed at a commercial nursery in Kfar Hess, Israel in April of 2012 and has shown that the unique features of this cultivar are stable and reproduced true to type in at least 4 successive generations.

SUMMARY OF THE INVENTION

The cultivar 'REY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'REY'. These characteristics in combination distinguish 'REY' as a new and distinct *Chamelaucium×Verticordia* cultivar:

1. Unique lanceolate foliage
2. Bright pink petals
3. Five lobed hypanthium

4. Distinctive ciliate sepals
5. Long pistil

PARENT COMPARISON

Plants of the new cultivar 'REY' are similar to plants of the seed parent in most horticultural characteristics, however, plants of the new cultivar 'REY' differ in the following:

1. Foliage shape; foliage of the new variety is lanceolate, foliage of the seed parent is needlelike.
2. Petal color of the new variety is bright pink, petal color of the seed parent is white.
3. The new variety has a larger sepal, with an incised margin, the seed parent has no incision in the sepal margin.
4. Pistil length of the new variety is longer than the pistil of the seed parent.
5. The new variety has a hypanthium with 5 definite lobes, the parent variety has a hypanthium without lobes.

Plants of the new cultivar 'REY' are similar to plants of the pollen parent in most horticultural characteristics, however, plants of the new cultivar 'REY' differ in the following:

1. Foliage shape; foliage of the new variety is lanceolate, foliage of the pollen parent is round.
2. Petal ,color of the new variety is bright pink, petal color of the pollen parent is red.
3. Pistil length of the new variety is shorter than the pistil of the pollen parent.
4. Sepals of the new variety are shorter, with a shorter marginal incision.

COMMERCIAL COMPARISON

Plants of the new cultivar 'REY' are comparable to the variety *Chamelaucium uncinatum* 'RotemWax', U.S. Plant Pat. No. 26,024. The two varieties are similar in some horticultural characteristics; however, the new variety 'REY' differs in the following:

1. Foliage shape; foliage of the new variety is lanceolate, foliage of this comparator is needlelike.

2. Petal color of the new variety is brighter pink than petal color of this comparator.
3. The new variety has distinctive ciliate sepals, this comparator has sepals fused into a single structure, with an entire margin, with a single incision.
4. The new variety has a hypanthium with 5 definite lobes, this comparator has a hypanthium without lobes.

Plants of the new cultivar 'REY' can also be compared to the unpatented *Verticordia monadelpha*. These plants are similar in some horticultural characteristics however, the new variety 'REY' differs in the following:

1. Foliage shape; foliage of the new variety is lanceolate, foliage of this comparator is needlelike.
2. Inflorescence type of the new variety is a terminal panicle, inflorescence of this comparator is corymbose.
3. The comparator has longer cilia structures emerging from the sepals.
4. Plants of the new variety are more upright and dense, compared to the globular, loose and spreading plant form of this comparator.

BRIEF DESCRIPTION OF THE PHOTOGRAPHS

The accompanying photograph in FIG. 1 illustrates in full color a close up of typical flowers and foliage of 'REY' at approximately 1 year of age.

Figure 2:
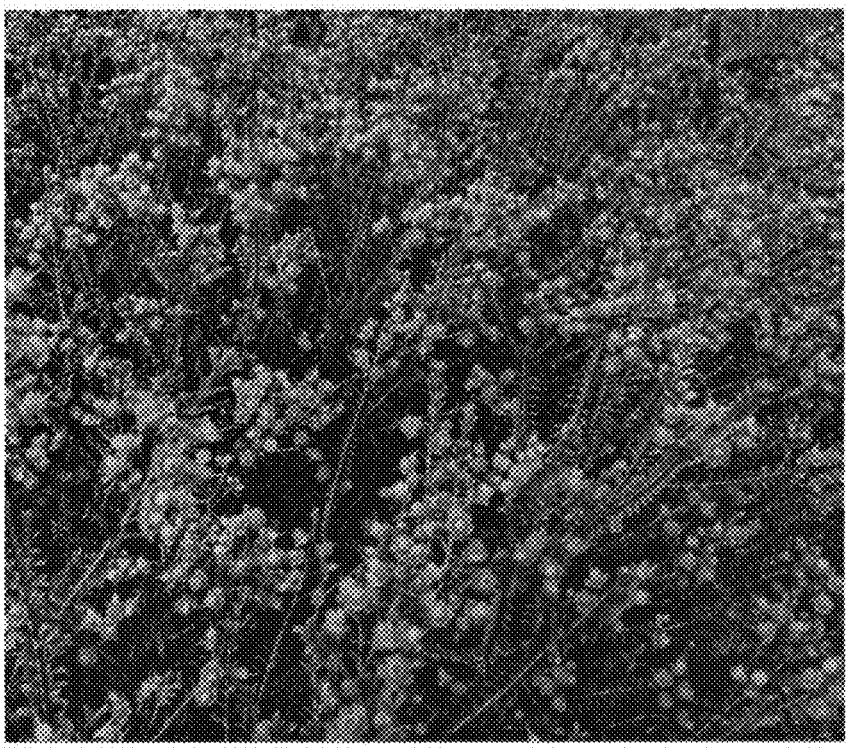

FIG. 2 illustrates plants of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'REY' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum*×*Verticordia grandis* 'REY'.

Age of plant described: At least 2 months old from a rooted cutting.

Typical flowering stems harvested per plant: 120 to 150 during the course of the season.

Vase life of flowers: Two weeks.

PROPAGATION

Time to produce a rooted plantlet: 30 to 60 days at approximately 24° C.

Root description: Fibrous, well branched.

PLANT

Growth habit: Upright plant produces multiple stems from a pinch, or after harvesting stems.

Height: 150 cm.

Plant spread: 80 cm.

Growth rate: Rapid.

Branching characteristics: Moderate to high branching occurs after pinching.

Length of primary lateral branches: 60 cm to 120 cm on average.

Diameter of lateral branches: 0.5 to 0.25 cm.

Quantity of primary lateral branches: 30 to 50, these are the harvested flowering stems.

Characteristics of primary lateral branches:

*Form*.—Round.
*Diameter*.—0.4 to 0.5 cm.
*Color*.—Near RHS Grey-Green 197A.
*Texture*.—Somewhat rough.
*Strength*.—Stems somewhat brittle.

Internode length: Range from 1.0 to 1.7 cm (measured in the top 20 cm of branch).

FOLIAGE

Leaf:

*Arrangement*.—Opposite.
*Quantity*.—Approximately 16 leaves, in the 10-15 cm section from the top of the branch.
*Average length*.—1.5 cm.
*Average width*.—0.7 cm.
*Shape of blade*.—Lanceolate.
*Apex*.—Acute.
*Base*.—Attenuate.
*Margin*.—Entire.
*Texture*.—Glabrous all surfaces.
*Pubescence*.—None.
*Aspect*.—Slightly reflexed back, occurring at approximately 15 degree angle from stem.
*Color*.—Young foliage upper side: Near RHS Yellow-Green 144A. Young foliage under side: Near RHS Yellow-Green 144A. Mature foliage upper side: Near RHS Green 137A. Mature foliage under side: Near RHS Green 137A.
*Venation*.—Indistinguishable from foliage.
*Petiole*.—Not present.

FLOWER

Natural flowering season: Winter until early Spring. Plants flower continuously under short day conditions.

Days to flowering from rooted cutting: Dependent upon short day photoperiod, not age, no juvenility.

Inflorescence type: Terminal panicle.

Individual flower type: Single, rotate 5 petaled with an obconical hypanthium. Flowers outwardly and upwardly facing.

Persistent or self-cleaning: Self-Cleaning.

Lastingness: About 2 weeks in a vase. Approximately 70 to 75 days on the plant.

Bud:

*Shape*.—Oblong.
*Length*.—0.6 cm.
*Diameter*.—0.5 cm.
*Color*.—Near RHS Red 45A.

Inflorescence size:

*Diameter*.—Average 10 cm.
*Length*.—Average 20 to 25 cm.

Flower size:

*Diameter*.—Average 1.0 cm.
*Length*.—Average 1.5 cm.

Corolla:

*Petals*.—Arrangement: Rotate, not overlapping. Length: Average 0.6 cm. Diameter: Average 0.5 cm. Quantity: 5. Texture: Smooth. Apex: Obtuse rounded. Base: Fused into a hypanthium.

Color:

*When opening*.—Upper surface: Near RHS Red 52B. Lower surface: Near RHS Red 52B.

*Fully opened*.—Upper surface: Near RHS Red-Purple 58B. Lower surface: Near RHS Red-Purple 58B.

*Aging*.—Upper surface: Near RHS Red-Purple 58B. Lower surface: Near RHS Red-Purple 58B.

Interior corolla/tube:

*Diameter*.—0.8 cm.

*Length*.—0.5 cm.

Color:

*When opening*.—Upper surface: Near RHS White N155B. Lower surface: Near RHS Yellow 4A.

*Fully opened*.—Upper surface: Near RHS Yellow-Green 151D. Lower surface: Near RHS Yellow 2C.

*Aging*.—Upper surface: Near RHS Red-Purple 69C. Lower surface: Near RHS Yellow-Green 152B.

Hypanthium:

*Diameter*.—Average 0.7 cm.

*Length*.—Average 0.5 cm.

*Shape*.—Obconical.

*Color*.—When opening: Inner surface: Near RHS Yellow-Green 144C. Outer surface: Near RHS Yellow-Green 152C. Fully opened: Inner surface: Near RHS Yellow-Green 146C. Outer surface: Near RHS Greyed-Red 181C.

Calyx/sepals:

*Quantity per flower*.—5.

*Shape*.—Ciliate.

*Length*.—0.5 cm.

*Width*.—0.7 cm.

*Apex*.—Ciliate.

*Base*.—Fused.

*Margin*.—Entire.

*Texture*.—Smooth.

*Color*.—Opening: Near Red-Purple 58B. Mature: Near Red 53C. Aging: Near Red 53C.

Peduncle: Peduncle consists of the plant stem.

Pedicel:

*Length*.—1.0 cm.

*Diameter*.—0.09 cm.

*Color*.—Near RHS Yellow-Green 152D.

Fragrance: None.

REPRODUCTIVE ORGANS

Stamens:

*Number*.—10.

*Filament length*.—2 mm.

*Filament color*.—Near RHS Green-Yellow 1B.

Anthers:

*Shape*.—Oval.

*Length*.—0.25 mm.

*Width*.—0.2 mm.

*Color*.—Near RHS Yellow-Orange 22A.

Pollen: Not observed.

Pistil:

*Number*.—1.

*Length*.—2 cm. Style Length: 0.4 cm. Style color: Near RHS Red-Purple 71A.

*Stigma*.—Shape: Round. Color: Near RHS Purple N79C. Texture: Glabrous.

OTHER CHARACTERISTICS

Seeds and fruits: Plants have not been observed to produce seeds or fruits.

Disease/pest resistance: Neither resistance nor susceptibility to the normal diseases and pests of *Chamelaucium* and *Verticordia* have been observed to date.

Temperature tolerance: From −2° C. to 35° C.

Drought tolerance: Very good tolerance for drought.

What is claimed is:

1. A new and distinct cultivar of *Chamelaucium*×*Verticordia* plant named 'REY' as herein illustrated and described.

* * * * *